United States Patent
Fischer

(10) Patent No.: US 7,195,485 B2
(45) Date of Patent: Mar. 27, 2007

(54) KITS FOR PLACEMENT OF A DENTAL POST

(75) Inventor: Dan E. Fischer, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 46 days.

(21) Appl. No.: 11/097,512

(22) Filed: Apr. 1, 2005

(65) Prior Publication Data

US 2006/0223034 A1    Oct. 5, 2006

(51) Int. Cl.
*A61B 19/02*    (2006.01)
(52) U.S. Cl. ................. 433/224; 433/50; 433/102; 206/369
(58) Field of Classification Search ......... 433/81, 433/49, 50, 102, 224; 206/63.5, 369
See application file for complete search history.

(56) References Cited

U.S. PATENT DOCUMENTS

| | | | |
|---|---|---|---|
| 3,358,826 A | 12/1967 | Siegel | 206/63.5 |
| 3,660,901 A | 5/1972 | Inoue | 32/40 |
| 4,293,074 A | 10/1981 | Dunsky | 206/572 |
| 4,327,060 A * | 4/1982 | Nisii | 422/300 |
| 4,353,694 A | 10/1982 | Pelerin | 433/77 |
| 4,850,866 A | 7/1989 | Gutierrez et al. | 433/72 |
| 5,127,832 A | 7/1992 | Zdarsky | 433/102 |
| 5,150,788 A * | 9/1992 | Weissman | 206/369 |
| 5,358,112 A * | 10/1994 | Gardner | 206/369 |
| 5,453,010 A * | 9/1995 | Klein | 433/221 |
| 5,516,287 A | 5/1996 | Zdarsky | 433/102 |
| 5,692,609 A * | 12/1997 | Lin | 206/368 |
| 5,829,590 A * | 11/1998 | Klein | 206/369 |
| 5,921,775 A * | 7/1999 | Buchanan | 433/102 |
| 5,964,592 A | 10/1999 | Hites et al. | 433/221 |
| 5,967,778 A * | 10/1999 | Riitano | 433/77 |
| 6,024,565 A | 2/2000 | Sicurelli et al. | 433/102 |
| 6,331,112 B1 | 12/2001 | Lee | 433/102 |
| 6,681,925 B2 * | 1/2004 | Fischer et al. | 206/63.5 |
| 6,827,576 B2 | 12/2004 | Karmaker et al. | 433/220 |
| 2004/0081940 A1 | 4/2004 | Roetzer et al. | 433/165 |

OTHER PUBLICATIONS

EDS Product Packaging "Flexi-Post" system URL: http://www.edsdental.com/productpdfs/fpostprofile.pdf.

* cited by examiner

*Primary Examiner*—Ralph A. Lewis
(74) *Attorney, Agent, or Firm*—Workman Nydegger

(57) ABSTRACT

A dental kit for use in placing a dental post in a prepared recess (e.g., a root canal) of a person's tooth. The dental kit includes a finishing drill, a plurality of permanent dental posts, a dental post analog, and optionally, a starter drill. The kit also includes a container having an interior, means for suspending the kit components within the container, and a removable lid.

22 Claims, 8 Drawing Sheets

KITS FOR PLACEMENT OF A DENTAL POST

BACKGROUND OF THE INVENTION

1. The Field of the Invention

The present invention is in the field of endodontics. More particularly, the invention relates to the placement of dental posts used during placement of a crown or other dental prosthesis onto a patient's tooth.

2. The Relevant Technology

When performing a root canal, the dental practitioner will remove the pulp material forming the nerve of the tooth at issue, carefully prepare the canal that contained the nerve material, and other pulp tissues, obturate or fill and seal the canal, and later insert a dental post into the root. The dental post serves to provide support for the coronal aspect of the tooth.

In determining which dental post to install, the dental practitioner considers the length, taper, and size required. In addition, the size of the drills used in preparing a post preparation depends on the size of the post to be placed.

In view of the foregoing, there is an ongoing need for kits and methods which would simplify the process of placing a dental post.

BRIEF SUMMARY OF THE PREFERRED EMBODIMENTS

The present invention is directed to a dental kit for use in placing a dental post in a prepared recess (e.g., a root canal) of a person's tooth. The dental kit includes a finishing drill, one or more permanent dental posts, a dental post analog, and optionally, one or more starter drills. The kit also includes a container having an interior, means for suspending (e.g., a foam material, molded plastic with through-holes, or other suspending, holding and/or organizing structure) the kit components within the container, and a tethered or removable lid.

One example of the finishing drill may include a metallic shaft having a proximal portion and a distal cutting portion, a smooth heat generating tip at the end of the distal portion, and a central abrasive portion between the proximal end and the distal end. In use, the finishing drill is configured to form a bore at least approximately corresponding to the size, shape, and length of a selected permanent dental post.

Each permanent dental post included within the kit includes a distal insertion portion for insertion into a prepared recess of a tooth and a proximal portion extending beyond the distal insertion portion. Permanent dental posts may be formed of any suitable material. According to one embodiment the permanent dental posts comprise a metal or fiber material (e.g., carbon or quartz fiber composite).

The dental post analog includes an analog post body with a distal insertion portion and a proximal portion extending beyond the distal insertion portion. The distal insertion portion at least approximately corresponds to the size, shape, and length of a selected permanent dental post. The dental post analog is configured for temporary insertion into a recess of a tooth (e.g., a prepared root canal).

The dental kit may be used for placing a dental post within a prepared recess of a tooth. According to one embodiment, a dental practitioner uses a finishing drill to prepare a recess of a tooth for insertion of a dental post. If provided, the dental practitioner may use a starter drill to remove the coronal gutta-percha within the packed and sealed tooth recess, to make an initial enlargement of the canal, prior to use of the finishing drill. The dental practitioner then inserts a permanent dental post into the prepared recess of a tooth. If desired, the dental post analog may be used as a try-in to verify or determine the correct size, girth, and length of permanent dental post to be used, prior to inserting the permanent dental post. Once a permanent dental post has been inserted into the prepared tooth recess, a core and dental prosthesis may be formed and fitted over the inserted permanent dental post.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention is directed to a dental kit for use in placing a dental post in a person's tooth. The kit includes a finishing drill, one or more permanent dental posts, a dental post analog, and optionally, a starter drill. The kit also includes a container having an interior, means for suspending (e.g., a foam material, molded plastic with through-holes, or other suspending, holding and/or organizing structure) the kit components within the container, and a tethered or removable lid.

II. Exemplary Dental Kits for Dental Surgery

Figure 1:
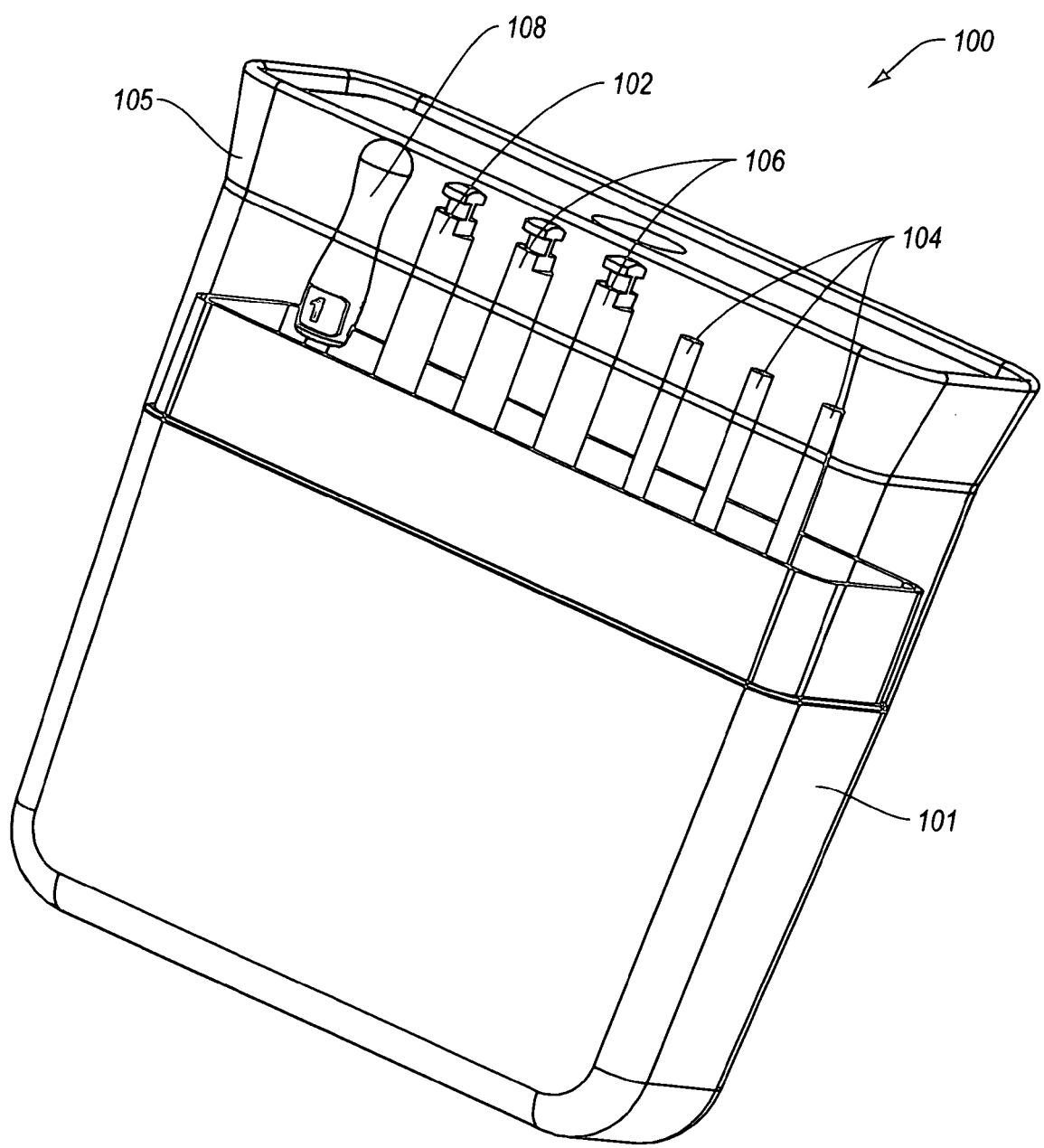
FIG. 1 is a perspective view of an exemplary dental kit.

FIG. 1 illustrates an exemplary dental kit 100. Dental kit 100 includes a container 101 having an interior, a foam material (not shown) for suspending and maintaining the contents of dental kit 100 within container 101, and a removable lid 105. Illustrated dental kit 100 includes one finishing drill 102, three permanent dental posts 104, two optional starter drills 106, and a dental post analog 108. Although illustrated with specific numbers of the various components (e.g., one finishing drill, three permanent dental posts, two starter drills, and one dental post analog), any number of each may be provided, as desired.

A. An Exemplary Finishing Drill

Figure 2A:
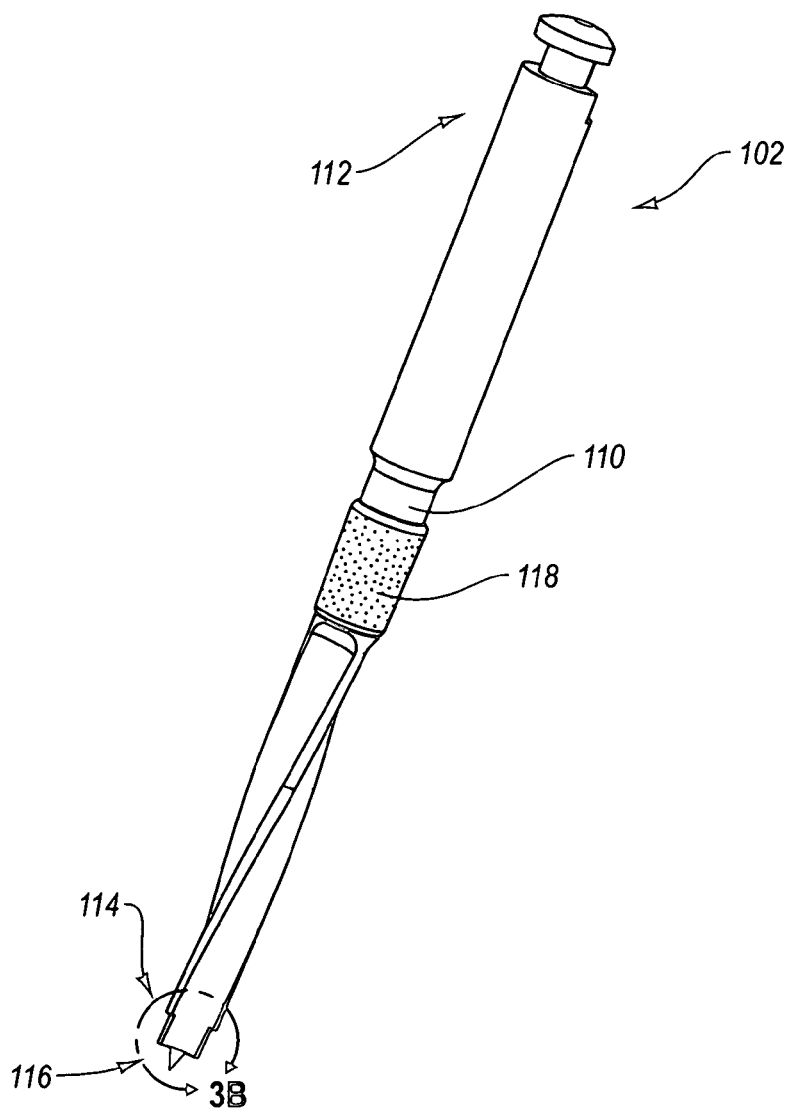
FIG. 2A is a perspective view of an exemplary finishing drill.
Figure 2B:
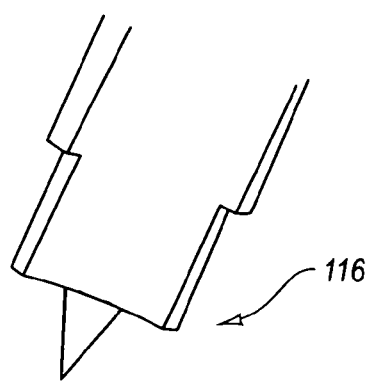
FIG. 2B is a close up perspective view of the distal tip of the finishing drill of FIG. 2A.

FIGS. 2A and 2B illustrate an exemplary finishing drill 102. Finishing drill 102 includes a metallic shaft 110 having a proximal portion 112 configured for attachment to a dental head piece, and a distal cutting portion 114. Finishing drill 102 also includes a smooth heat generating tip 116 (shown in close up in FIG. 2B) at the end of distal portion 114 and a central abrasive portion 118 located between proximal portion 112 and distal cutting portion 114. In use, finishing drill 102 is configured to form a bore that at least approximately corresponds to the size, shape, and length of at least one of the permanent dental posts included within dental kit 100.

FIG. 2B illustrates a close up perspective view of heat generating tip 116. Additional details regarding heat generating tip 116, and exemplary embodiments of finishing drills are disclosed in United States Patent Application Publication 2004/0081940, herein incorporated by reference with respect to its disclosure of finishing drills. Exemplary finishing drills are sold under the trade name GYROTIP by MTI Precision Products LLC, located in Lakewood, N.J.

B. An Exemplary Permanent Dental Post

Figure 3:
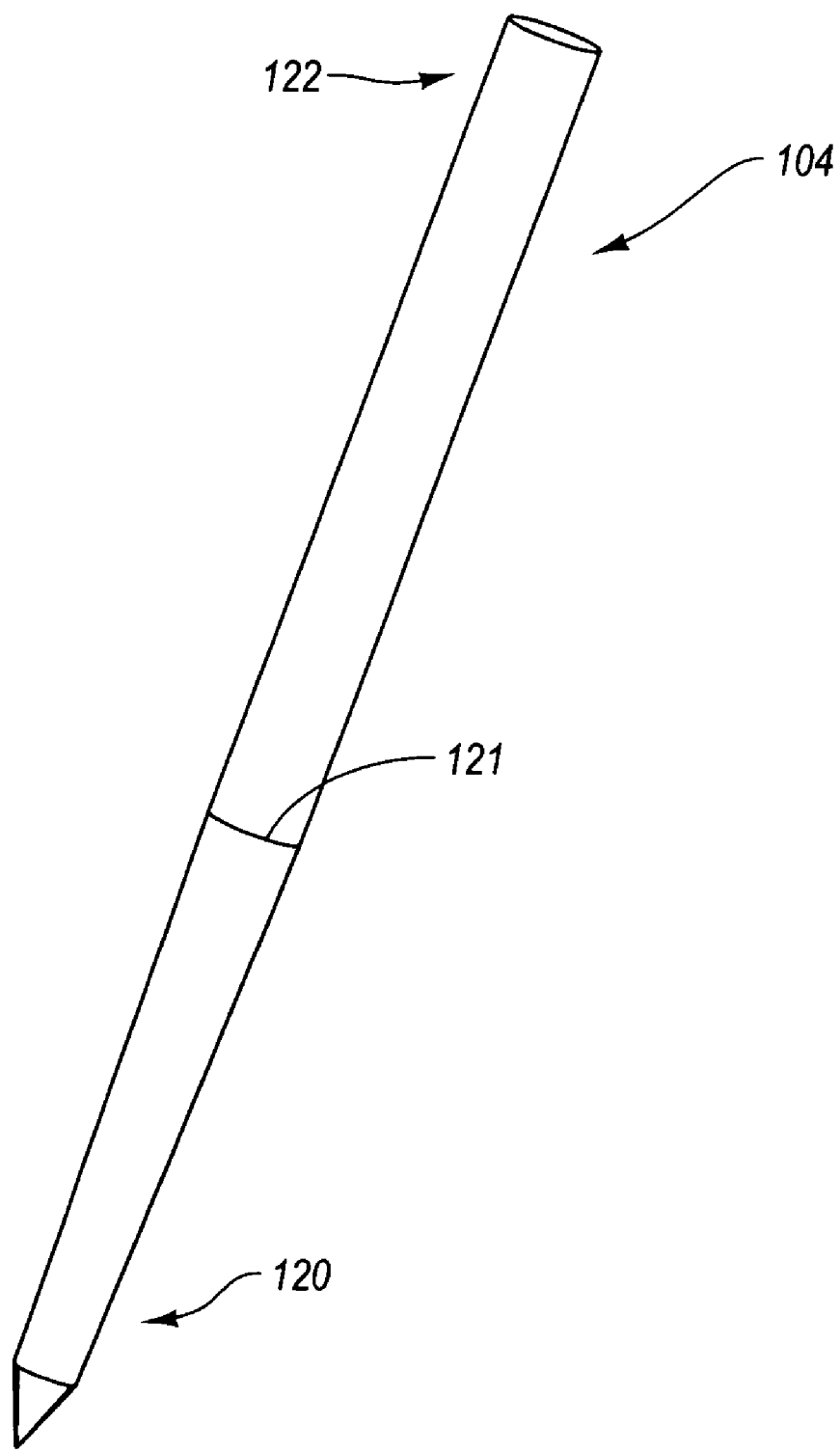
FIG. 3 is a perspective view of an exemplary permanent dental post.

FIG. 3 illustrates one embodiment of an exemplary permanent dental post 104. Permanent dental post 104 includes a distal insertion portion 120 for insertion into a prepared recess of a tooth (e.g., a root canal). Permanent dental post 104 also includes a proximal portion 122 which extends beyond distal insertion portion 120. The distal insertion portion 120 includes a tapered portion (beginning at 121) and a non-tapered parallel portion which extends up through proximal portion 122.

Permanent dental posts included in the dental kits of the present invention may comprise any suitable material. According to one preferred embodiment, permanent dental post 104 comprises a metal or fiber material (e.g., carbon or quartz fiber composite). Exemplary permanent dental posts are sold by RTD, located in Grenoble, France.

C. An Exemplary Starter Drill

Figure 4:
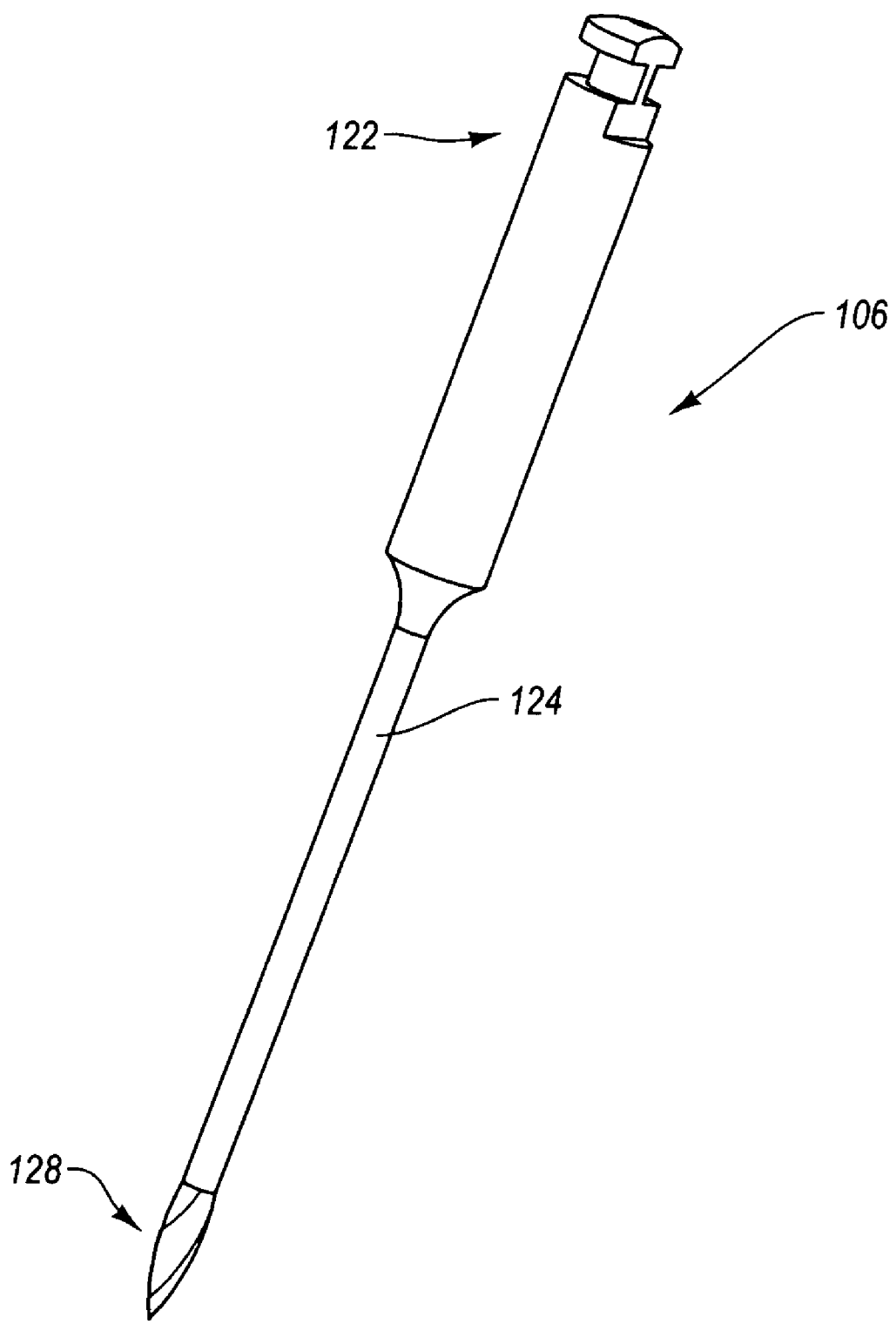
FIG. 4 is a perspective view of an exemplary starter drill.

FIG. 4 illustrates an exemplary starter drill 106. Exemplary starter drill 106 includes a metallic shaft 124 having a proximal portion 126 configured for attachment to a dental head piece, and a distal cutting portion 128, which may be bulbous, as illustrated. Starter drill 106 may be useful for removing coronal gutta-percha prior to use of finishing drill 102. Exemplary starter drills (e.g., Gates Glidden drills) are sold by Brasseler USA, located in Savannah, Ga.

D. An Exemplary Dental Post Analog

Figure 5:
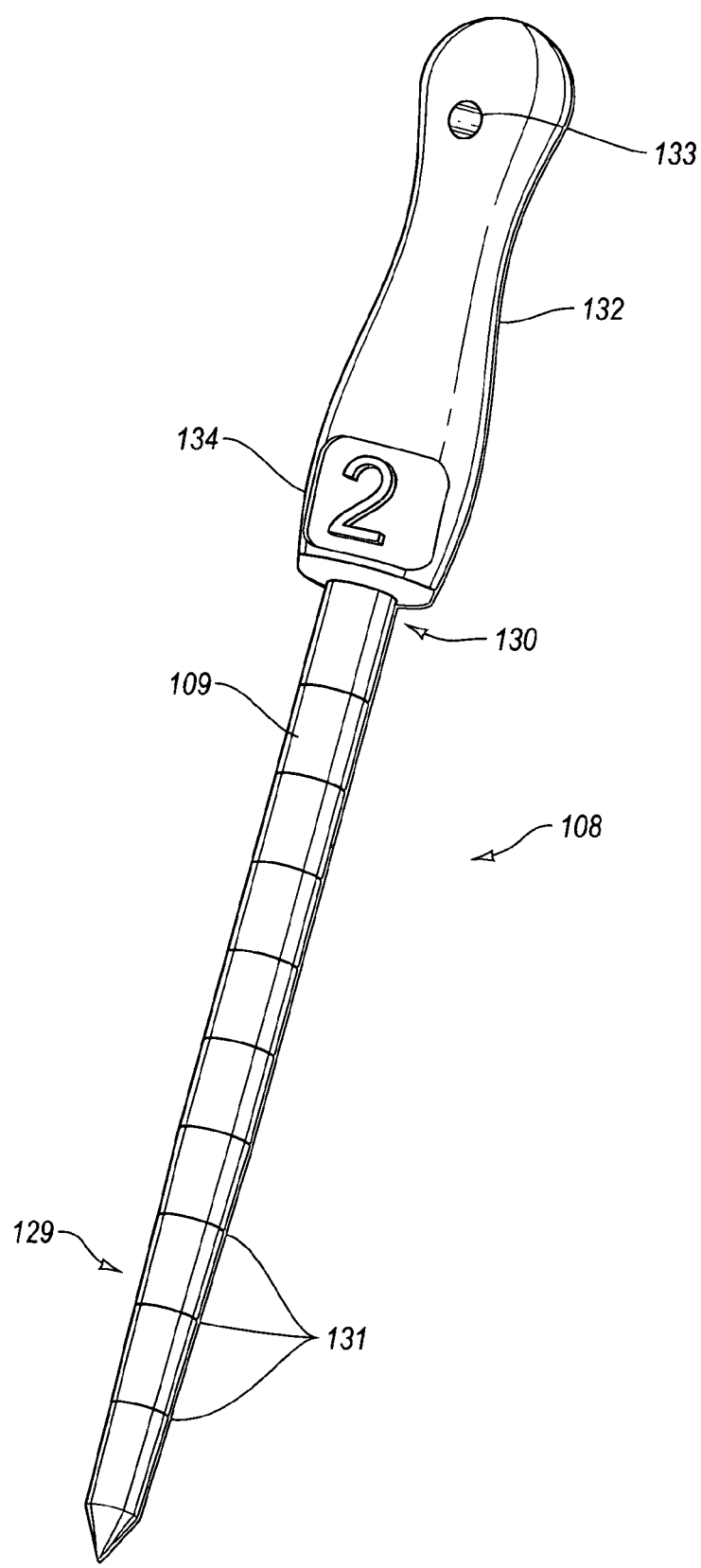
FIG. 5 is a perspective view of an exemplary dental post analog.

FIG. 5 illustrates an exemplary dental post analog 108. Dental post analog 108 includes an analog post body 109. Post body 109 includes a distal insertion portion 129 and a proximal portion 130 extending beyond distal insertion portion 129. The distal insertion portion 129 at least approximately corresponds in size, shape (including taper), and length to a permanent dental post (e.g., permanent dental post 104). Distal insertion portion 129 is configured for temporary insertion into a prepared recess of a tooth.

Analog post body 109 also includes at least one of means for determining the depth of placement of the distal insertion portion, means for gripping the post body, or means for tethering the post body. The illustrated embodiment of dental post analog 108 includes markings 131 formed along distal insertion portion 129. Markings 131 are one example of means for determining the depth of placement of the distal insertion portion. Alternative examples of means for determining the depth of placement of the distal insertion portion include one or more circumferential grooves formed within the distal insertion portion or one or more circumferential ridges formed on the distal insertion portion.

Dental post analog 108 may include means for gripping analog post body 109. The embodiment illustrated in FIG. 5 includes a handle 132 formed near a proximal end of proximal portion 130 of post body 109. Handle 132 is one example of means for gripping analog post body 109.

Dental post analog 108 may also include means for tethering post body 109. The embodiment illustrated in FIG. 5 includes a hole 133 formed through the proximal portion of handle 132. A string or other flexible leash can be inserted into hole 133 for tethering post body 109 as a safety measure (e.g., to prevent inadvertent swallowing of or chocking on post body 109). Hole 133 is one example of means for tethering post body 109.

Dental post analog 108 may include coding means for identifying the size of dental post analog 108. Number 134 is one example of means for coding. A letter or other marking may alternatively be used. In some cases, coding means for identifying the size of dental post analog 108 may comprise forming at least a portion of post body 109 so as to be of a selected color, (e.g., yellow may signify the smallest size, red and blue may signify or identify intermediate sizes, while green may signify a largest size).

The dental post analogs may be formed from any suitable material. Exemplary materials include, but are not limited to, thermoplastic materials, thermoset materials, ceramics, or metals.

According to one embodiment, at least the distal insertion portion 129 of post body 109 may be formed of a material that is radiopaque. Such an embodiment allows a dental practitioner to see the location of a dental post analog while inserted into a prepared recess of a tooth by x-ray or other radiograph.

The contents of each dental kit, including the finishing drill, any optional starter drills, the dental post analogs, and even the permanent dental posts may be autoclavable, so as to allow for cleaning and reuse of the dental kit components. Alternatively, the dental kit and its contents may be disposable.

III. Exemplary Methods of Use

Figure 6:
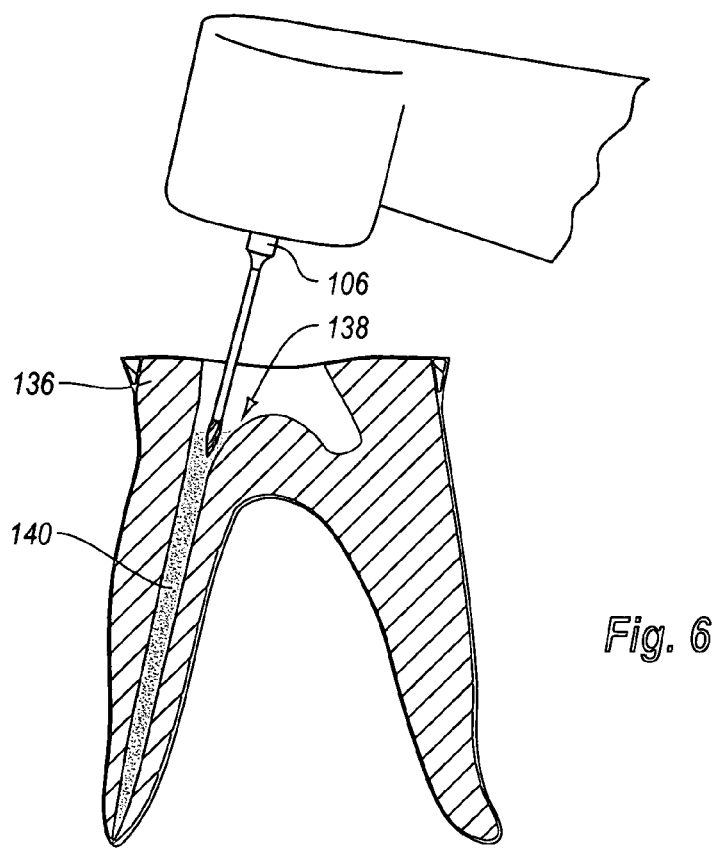
FIG. 6 illustrates use of the starter drill of FIG. 4 to remove coronal gutta-percha from a packed and sealed recess of a tooth prior to insertion of a dental post.

FIG. 6 illustrates a tooth 136 which has been broken down in preparation for fitting of a dental prosthesis (e.g., a crown). Prepared tooth recess 138 (e.g., a root canal) has been reamed out to remove nerve and other tissue, while also increasing the size of recess 138 in preparation to installing a dental post and dental prosthesis. The tooth recess 138 has also been packed and sealed with packing material 140 (e.g., gutta-percha).

Figure 7:
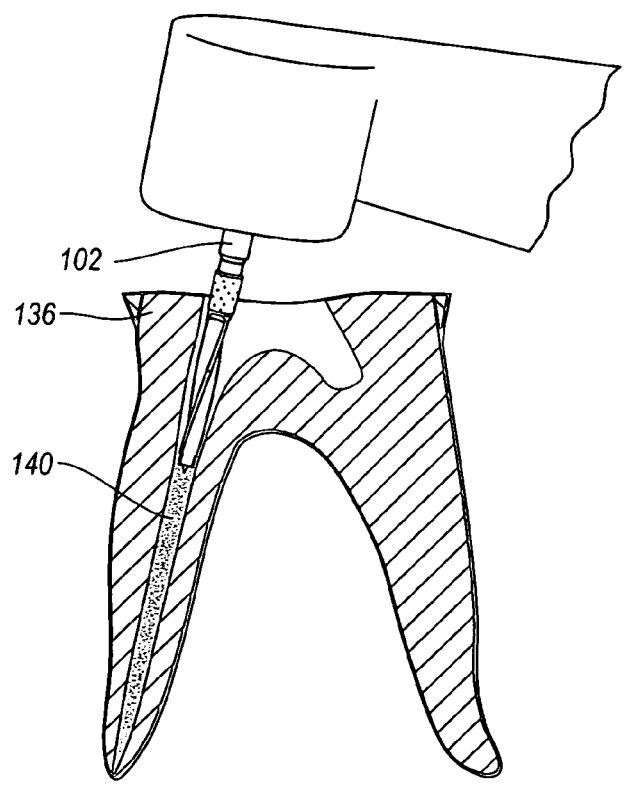
FIG. 7 illustrates use of the finishing drill of FIG. 2A to remove gutta percha and widen the root canal so as to prepare the canal for insertion of a dental post.

In order to prepare tooth recess 138 for insertion of a permanent dental post, starter drill 106 may be used to remove the coronal gutta-percha or other packing material 140 down to the root canal orifice. Once the coronal gutta-percha has been removed, a finishing drill 102 may be used to remove additional packing material, while slightly widening the width of recess 138 down to a desired depth as illustrated in FIG. 7. The removal of packing material 140, and slight widening and shaping of tooth recess 138 prepares recess 138 to receive a permanent dental post. Use of starter drill 106 is optional, i.e., finishing drill 102 may be used to remove any needed packing material 140, without the use of starter drill 106.

Figure 8A:
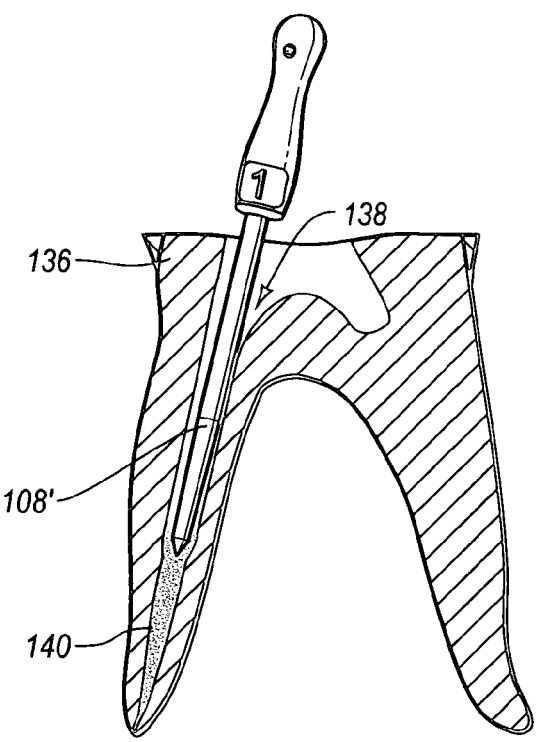
FIGS. 8A–8B illustrate a method of using a dental post analog as a try-in for a permanent dental post.
Figure 8B:
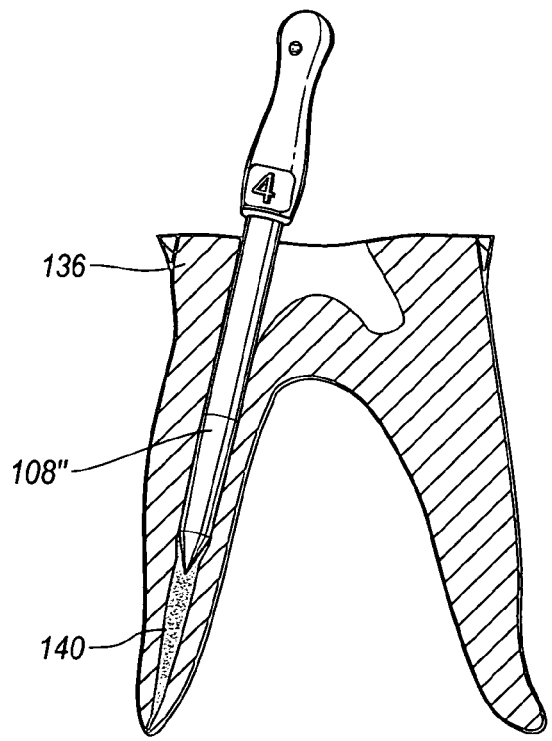
Figure 9:
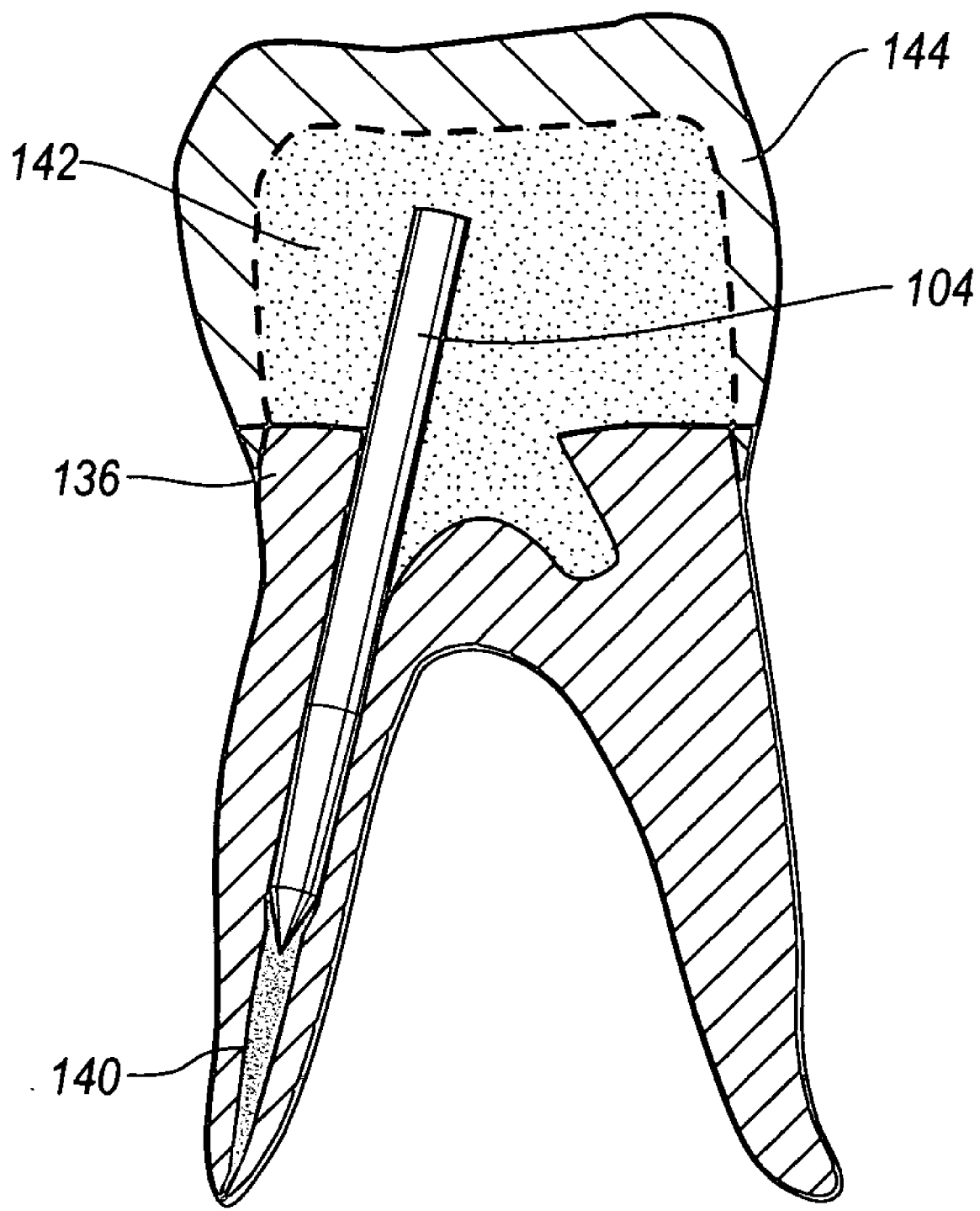
FIG. 9 illustrates a completed dental restoration including a permanent dental post, a core, and a crown.

As illustrated in FIGS. 8A and 8B the dental post analog or analogs may be used as a try-in for determining the size, girth, and length of a correctly sized permanent dental post. In this procedure, a dental practitioner selects a dental post analog of a desired size, girth, and length, and as illustrated in FIG. 8A, the dental post analog 108' is inserted into prepared tooth recess 138 of tooth 136 on a trial basis to determine whether inserted dental post analog 108' corresponds to a correctly sized permanent dental post. FIG. 8A illustrates insertion of a dental post analog 108' which is too narrow. The dental practitioner may continue to insert incrementally larger sized dental post analogs until the correctly sized post analog is identified. FIG. 8B illustrates insertion of a thicker dental post analog 108", which is correctly sized with respect to tooth recess 138. Using one or more dental post analogs as try-ins aids the dental practitioner in determining which size of permanent dental post should be used. Use of the dental post analogs allows the dental practitioner to do so inexpensively and conveniently with a disposable or autoclavable dental post analog. In addition, the procedure can be performed without contaminating the permanent dental posts during a try-in procedure. Once removed, the dental post analog may either be discarded or autoclaved, as desired.

A dental prosthesis 144 (e.g., a crown) and supporting core 142 may then be formed, fitted, and bonded, cemented, or otherwise placed over inserted permanent dental post 104. Methods for forming and placing a supporting core 142 and a dental prosthesis 144 will be known to those skilled in the art. Additional methods for forming and placing a core and dental prosthesis employing the dental post analogs included in the dental kit are disclosed in U.S. application Ser. No. 11/094,991, filed Mar. 31, 2005, hereby incorporated by reference in its entirety.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental kit for placement of a dental post in a person's tooth comprising:
    a container having an interior, means for suspending kit components within the container, and a tethered or removable lid;
    a finishing drill comprised of:
        a metallic shaft, said shaft having a proximal portion and a distal cutting portion;
        in use said finishing drill forming a bore at least approximately corresponding to the size, shape, and length of a selected permanent dental post;
    at least one permanent dental post, comprising a distal insertion portion for insertion into a recess of a tooth and a proximal portion extending beyond the distal insertion portion; and
    at least one dental post analog, which is separate from the at least one permanent dental post and designed to facilitate verification or determination of a correct size, girth and length of a selected permanent dental post prior to inserting the selected permanent dental post into a recess of a tooth, and which includes one or more properties or features that render it unsuitable for use as a permanent dental post, comprising an analog post body comprising:
        a distal insertion portion, at least approximately corresponding to the size, shape, and length of the selected permanent dental post, for temporary insertion into a recess of a tooth;
        a proximal portion extending beyond said distal insertion portion.

2. A dental kit as recited in claim 1, further comprising at least one starter drill.

3. A dental kit as recited in claim 1, wherein each of said permanent dental posts comprises a metal or fiber material.

4. A dental kit as recited in claim 1, wherein each of said permanent dental posts comprises a carbon or quartz fiber composite material.

5. A dental kit as recited in claim 1, wherein each of said dental post analogs comprises at least one of a thermoplastic material, a thermoset material, a ceramic, or a metal.

6. A dental kit as recited in claim 1, wherein at least said distal insertion portion of said post body is radiopaque.

7. A dental kit as recited in claim 1, wherein said analog post body comprises means for determining a depth of placement of said distal insertion portion, said means for determining a depth of placement of the distal insertion portion comprising one or more of circumferential grooves, ridges, or markings formed within said distal insertion portion.

8. A dental kit as recited in claim 1, wherein said dental post analog comprises means for gripping said post body, said means for gripping said post body comprising a handle formed near a proximal end of said proximal portion of said post body.

9. A dental kit as recited in claim 1, wherein said dental post analog comprises means for tethering said post body, said means for tethering said post body comprising a hole formed through the proximal portion of said post body.

10. A dental kit as recited in claim 1, further comprising coding means for identifying the size of said dental post analog, said coding means comprising one of a number, a letter, or other marking on the post body.

11. A dental kit as recited in claim 1, further comprising coding means for identifying the size of said dental post analog, said coding means comprising forming at least a portion of the analog post body so as be of a selected color.

12. A dental kit as recited in claim 1, wherein said kit is disposable.

13. A dental kit as recited in claim 1, wherein said kit is autoclavable.

14. A dental kit for placement of a dental post in a person's tooth comprising:
    a container having an interior, means for suspending kit components within the container, and a tethered or removable lid;
    a finishing drill comprised of:
        a metallic shaft, said shaft having a proximal portion and a distal cutting portion;
        a smooth, heat generating tip at the end of said distal portion;
        a central abrasive portion between said proximal end and said distal end; and
        in use said finishing drill forming a bore at least approximately corresponding to the size, shape, and length of a selected permanent dental post;

at least one permanent dental post, comprising a distal insertion portion for insertion into a recess of a tooth and a proximal portion extending beyond the distal insertion portion; and at least one dental post analog, which is separate from the at least one permanent dental post and designed to facilitate verification or determination of a correct size, girth and length of a selected permanent dental post prior to inserting the selected permanent dental post into a recess of a tooth, and which includes one or more properties or features that render it unsuitable for use as a permanent dental post, comprising an analog post body comprising:

a distal insertion portion, at least approximately corresponding to the size, shape, and length of a permanent dental post, for temporary insertion into a recess of a tooth; and a proximal portion extending beyond said distal insertion portion.

15. A method of using a dental kit for placement of a dental post, comprising:

providing a dental kit for placement of a dental post comprising:

a container having an interior, means for suspending kit components within the container, and a tethered or removable lid;

a finishing drill;

at least one permanent dental post comprising a distal insertion portion for insertion into a prepared recess of a tooth and a proximal portion extending beyond said distal insertion portion;

at least one dental post analog, which is separate from the at least one permanent dental post and designed to facilitate verification or determination of a correct size, girth and length of a selected permanent dental post prior to inserting the selected permanent dental post into a recess of a tooth, comprising an analog post body comprising:

a distal insertion portion, at least approximately corresponding to the size, shape, and length of a permanent dental post, for temporary insertion into a recess of a tooth; and a proximal portion extending beyond said distal insertion portion; and using said finishing drill to prepare a recess of a tooth for insertion of a dental post;

inserting a dental post analog into the recess in order to determine a correct size, girth and length of permanent dental post;

removing the dental post analog from the recess; and inserting a permanent dental post into said recess having the correct size, girth and length as determined by the dental post analog.

16. A method as recited in claim 15, wherein said recess of a tooth is within a root canal of the tooth.

17. A method as recited in claim 15, further comprising using a starter drill to remove coronal packing material from said recess of a tooth prior to using said finishing drill to complete preparation of said tooth recess.

18. A method as recited in claim 15, further comprising inserting said dental post analog into a prepared tooth recess on a trial basis to determine whether said inserted dental post analog corresponds in size to a correctly sized permanent dental post.

19. A method as recited in claim 18, wherein said dental post analog is inserted on a trial basis prior to inserting said permanent dental post.

20. A method as recited in claim 15, further comprising forming a core and bonding a dental prosthesis over said inserted permanent dental post.

21. A method as recited in claim 15, further comprising discarding the remainder of said kit.

22. A method as recited in claim 15, further comprising autoclaving the remainder of said kit.

* * * * *

UNITED STATES PATENT AND TRADEMARK OFFICE
CERTIFICATE OF CORRECTION

PATENT NO. : 7,195,485 B2 Page 1 of 1
APPLICATION NO. : 11/097512
DATED : March 27, 2007
INVENTOR(S) : Dan E. Fischer It is certified that error appears in the above-identified patent and that said Letters Patent is hereby corrected as shown below:

<u>Column 4</u>
Line 19, change "chocking" to --choking--

<u>Column 6</u>
Line 47, after "so as" insert --to--

Signed and Sealed this

Twentieth Day of November, 2007

JON W. DUDAS
*Director of the United States Patent and Trademark Office*